United States Patent [19]

Pettijohn et al.

[11] Patent Number: 5,705,725
[45] Date of Patent: Jan. 6, 1998

[54] AROMATIC ALKALI METAL ALKENE ADDITION PROCESS

[75] Inventors: Ted M. Pettijohn; Mark E. Lashier; Henry L. Hsieh, all of Bartlesville, Okla.

[73] Assignee: Phillips Petroleum Company, Bartlesville, Okla.

[21] Appl. No.: 770,004

[22] Filed: Oct. 2, 1991

[51] Int. Cl.[6] ............... C07C 2/66; C07C 2/68; C07C 2/34

[52] U.S. Cl. ............ 585/457; 585/466; 585/467; 585/511; 585/516

[58] Field of Search ................... 585/457, 466, 585/467, 511, 516; 502/152, 153; 260/665 R

[56] References Cited

U.S. PATENT DOCUMENTS

| | | |
|---|---|---|
| 2,721,885 | 10/1955 | Pines et al. ............... 585/457 |
| 3,223,742 | 12/1965 | Eberhardt . |
| 3,607,851 | 9/1971 | Forman . |
| 5,196,622 | 3/1993 | Pettijohn et al. ............... 585/457 |

FOREIGN PATENT DOCUMENTS 766215   1/1957   United Kingdom .

OTHER PUBLICATIONS

Eric K. Rideal, *Concepts in Catalysis*, Academic Press 1968 p. 5.
J. Polymer Science Part A–1 7: pp. 461–469 (1969) no month available.
Tetrahedron Letters No. 2 pp. 257–262 (1966) no month available.

*Primary Examiner*—Elizabeth D. Wood
*Attorney, Agent, or Firm*—Carl D. Corvin

[57] ABSTRACT

A process is provided comprising: (a) contacting a hydrocarbyl lithium with an alkali metal hydrocarbyloxide in the presence of an aromatic compound; and thereafter (b) recovering an aromatic alkali metal compound; and thereafter (c) contacting said aromatic alkali metal compound with an alpha-olefin. Optionally, a catalytic support is also present during steps a, b, and c.

14 Claims, No Drawings

AROMATIC ALKALI METAL ALKENE ADDITION PROCESS

BACKGROUND OF THE INVENTION

This invention relates to a process for the addition of an alkene to a aromatic alkali metal compound.

Alkylation, in general, is a process involving the addition of an alkyl group. Specifically, the term is used in the art to apply to various methods, including both thermal and catalytic processes, for bringing about the union of paraffinic hydrocarbons with olefins. Alkylation reactions are important throughout synthetic organic chemistry. For example, the process is especially effective in yielding gasolines of high octane number and low boiling range which are useable as aviation fuels.

Dimerization, in general, is a process involving the addition of an alkene to another alkene which has the same molecular structure. Dimerization processes are important in organic chemistry for a variety of reasons. For example, dimerization reactions are used to form higher alpha olefins from lower alpha olefins thereby providing higher molecular weight monomers which can then be polymerized. For example, propylene can be dimerized to form 4-methyl-1-pentene which in turn can be polymerized into poly(4-methyl-1-pentene). Currently, a preferred method in the art to perform dimerization reactions involves using an alkali metal on an alkali metal carbonate. However, these alkali metal/alkali metal carbonate catalyst systems tend to suffer from severe degradation which can lead to reactor plugging and shorter catalyst life. Additionally, it has been theorized that the conversion of an alkali metal to an active species can result in the expansion of the alkali metal in the alkali metal carbonate to the point that the catalytic system starts to break down. Therefore, methods to produce an active species without the use of an elemental alkali metal would be both scientifically and economically valuable.

SUMMARY OF THE INVENTION

It is an object of this invention to provide an improved alkene addition process.

It is another object of this invention to provide an improved dimerization process.

These and other objects of this invention will become apparent to those skilled in the art from the following detailed description of the invention.

In accordance with one embodiment of this invention, a process is provided comprising contacting a hydrocarbyl lithium with an alkali metal hydrocarbyloxide in the presence of an aromatic compound and at least one alpha-olefin. Optionally, a catalytic support is present during the contacting.

In another embodiment a process is provided comprising: (a) contacting a hydrocarbyl lithium with an alkali metal hydrocarbyloxide in the presence of an aromatic compound; and thereafter (b) recovering an aromatic alkali metal compound; and thereafter (c) contacting said aromatic alkali metal compound with an alpha-olefin. Optionally, a catalytic support is present during steps a, b, and c.

DETAILED DESCRIPTION OF THE INVENTION

In general, this invention comprises contacting an alpha-olefin with an aromatic alkali metal compound to form an addition product.

Alpha Olefin Reactants

The alpha olefin reactants that are applicable for use in this invention can be categorized by the following:
1) the alpha-olefin should have at least one double bond attached to the first carbon atom;
2) the alpha olefin should have between 2 and 20 carbon atoms inclusive in the molecule;
3) the alpha olefin cannot contain any oxygen atoms, acid groups, or conjugated double bonds;
4) the alpha olefin can be linear or branched.

Although not wanting to be bound by theory it has been theorized that those alpha olefins which have the above characteristics have the ability to form a semi-stable resonance group with an alkali metal. Examples of suitable alpha-olefins useful in this invention include, but are not limited to, ethylene, propylene, 1-butene, isobutylene, 3-methyl-1-butene, 1-pentene, 3-methyl-1-pentene, 4-methyl-1-pentene, 1-hexene, 3-ethyl-1-hexene, 1-octene, 1-decene, or mixtures thereof.

Aromatic Alkali Metal Compound

The organometallic compounds useful in this invention are those compounds comprising an aromatic group and an alkali metal. For the purposes of this specification the term "aromatic" is defined as follows. In one form the aromatic group can be methylbenzene. Other compounds which could be used are those which have a methylbenzene-like structure and/or which have substituents along the benzene ring. For example, the following compounds can be used: 1,2-dimethyl-benzene; 1,3-dimethyl-benzene; 1,4-dimethyl-benzene; and 1,3,5-trimethyl-benzene. In general the substituents should not contain any oxygen atoms, nor any acid groups, which could interfere with the reaction. Structures which tend to obey the above limitations generally have the following structural formula.

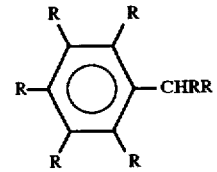

Wherein each R is independently selected from the group consisting of hydrogen, alkyl, aryl, and/or alkylaryl. This formula and the above compounds are given as examples only and are not meant to be unduly limiting of the reasonable scope of the vast numbers of compounds which can be used as the aromatic component. It has been theorized that an important constituent of the aromatic component is the formation of a substantially stable resonance group between the alkali metal compound, the aromatic ring, and the methyl-like substituents in the aromatic structure. Examples of aromatic alkali metal compounds useful in this invention are benzyl lithium ($C_6H_5CH_2Li$); benzyl sodium; benzyl potassium; benzyl cesium; and benzyl rubidium.

Procedures to Make an Aromatic Alkali Metal Compound

It is well known in the art that benzyl lithium can be formed by reacting benzylchloride or benzylbromide with metallic lithium. However, in order to make aromatic alkali metal groups other than aromatic lithium it is necessary to use a different process. In general, the process of forming aromatic alkali metal compounds, other than aromatic lithium, is accomplished in accordance with the invention by contacting a hydrocarbyl lithium compound with an alkali metal hydrocarbyloxide in the presence of an aromatic group. This reaction yields, in general, a hydrocarbon, lithium hydrocarbyloxide, and an aromatic alkali metal compound.

The hydrocarbyl lithium used in the above reaction can be characterized as follows. The hydrocarbyl group can be a linear or branched alkyl or aryl and can contain from 1 to 20 and most preferably from 2 to 12 carbon atoms in the molecule. However, the hydrocarbyl group must be non-reactive in an alkene addition reaction. This means, in general, that the hydrocarbyl group must not contain any oxygen atoms, nor any acid groups, which could interfere with the reaction. Examples of suitable hydrocarbyl lithium compounds useful in this invention are methyl lithium, ethyl lithium, propyl lithium, butyl lithium, pentyl lithium, hexyl lithium, or mixtures thereof. The mole ratio of hydrocarbyl lithium to alkali metal hydrocarbyloxide varies from a ratio of 20:1 down to 1:1.

The alkali metal hydrocarbyloxide can be characterized by the following. The hydrocarbyloxide can be a linear or branched alkyl or aryl and contain 1 to 20 carbon atoms and most preferably 2 to 12 carbon atoms in the molecule. Examples of alkali metal hydrocarbyloxides include, but are not limited to, potassium methoxide, potassium ethoxide, potassium propyloxide, potassium butoxide, and potassium pentoxide, sodium methoxide, sodium ethoxide, or mixtures thereof. It is also important that this hydrocarbyloxide be nonreactive in alkene addition reactions. This means, in general, that the hydrocarbyloxide cannot contain any oxygen atoms, besides the one connecting to the alkali metal, nor any acid groups, which could interfere with the reaction.

The reaction conditions to form these aromatic alkali metal compounds are as follows. The temperature of the reaction should be between about −50° C. to about 350° C., preferably 0° C. to 250° C., and most preferably 20° C. to 200° C. These temperature ranges are preferred due to such factors as the particular hydrocarbyl lithium and alkali metal hydrocarbyloxide used to form the aromatic alkali metal compound and the fact that as the temperature rises the rate of reaction will also rise. The pressure that the reaction can take place at is from about atmospheric to about 10,000 psig, preferably from atmospheric to about 2,000 psig and most preferably from atmospheric to about 1,000 psig. The higher the pressure the greater the rate of the reaction. Additionally, this reaction can take place in a solvent provided the solvent is relatively inert and free of compounds which would tend to interfere with the reaction. That is, the solvent should be substantially free of compounds which contain acid groups, water, or oxygen.

After the aromatic alkali metal compound is formed it can be used either in situ or it can be separated and stored for later use. The alpha olefin and the aromatic alkali metal compound can be reacted under the same conditions stated above for forming the aromatic alkali metal compound. An example of an in situ process would be the addition of n-butyl lithium and potassium tert-butoxide in an excess of toluene and propylene. In general, these compounds would react to yield n-butane, lithium tert-butoxide, benzyl potassium, 4-methyl-1-pentene, and isobutylbenzene which is the addition product of benzyl potassium and propylene. Additionally, some small quantities of trimers and tetramers of propylene might be formed.

An example of a two-step process would be using the reactants listed above without any propylene or at most a small amount of propylene. From this reaction a benzyl potassium compound would precipitate from solution thereby enabling recovery of benzyl potassium from the product formed. This benzyl potassium can then be used with an alpha-olefin to form an addition product. Specifically, if a molar excess of propylene (for example, a 10:1 molar ratio of propylene to benzyl potassium) is then added to the benzyl potassium, 4-methyl-1-pentene will be formed. Furthermore, as an additional example, if a slight amount of propylene is added to the benzyl potassium (for example a 1:10 molar ratio of propylene to benzyl potassium), isobutylbenzene will be formed.

Regardless of how the above reaction is conducted a catalytic support can be used in the reaction also. The term "catalytic support" is defined as a composition useful in increasing the entire catalytic system's productivity and value, it is not meant to be construed as an inert composition which lends nothing to the catalytic system. A catalytic support would allow the catalyst to precipitate on and/or impregnate the catalytic support. This would provide an improved catalytic system and reaction site. Examples of catalytic supports are alkali metal carbonates; silicas, aluminas, silica-aluminas, and alumina-phosphates. These catalytic supports are broadly known in the art and are disclosed, for example, in U.S. Pat. Nos. 4,544,790; 4,609, 637; 4,656,154; 4,982,043; 4,988,658; 5,001,204; 5,021, 379; and 5,026,796; which are hereby incorporated by reference. It is preferred that the catalytic supports be alkali metal carbonates and/or silica-aluminas, for best productivity and selectivity.

EXAMPLES

These examples are provided to further assist a person skilled in the art with understanding this invention. The particular reactants, conditions, and the like, are intended to be generally illustrative of this invention and are not meant to be construed as unduly limiting the reasonable scope of this invention.

Example I

Preparation and Analysis of a Benzyl Potassium Catalyst

In a sealed 250 mL glass bottle under anhydrous and oxygen free conditions a benzyl potassium catalyst was formed. The catalyst was prepared by dissolving 3.5 grams of potassium t-butoxide in 40 mL of hot (60° C.), anhydrous toluene. After the potassium t-butoxide was dissolved, 30 mL of 2 molar n-butyl lithium was added dropwise. Immediately a bright orange precipitate was formed. The precipitate was allowed to settle and the liquid was removed. Thereafter, the precipitate was washed three times with 100 mL of anhydrous cyclohexane in the glass bottle. After each wash the precipitate was allowed to settle before the liquid was removed. The glass bottle was then purged with dry nitrogen and then heated to about 100° C. This temperature was then maintained for about 1 hour. The bottle was then cooled with a dry nitrogen purge.

The benzyl potassium catalyst isolated above was analyzed for its composition. First, 1.1 grams of the catalyst was dissolved in 43.4 grams of n-propanol. Second, this solution was then analyzed by an inductively coupled plasma-atomic emission spectrometer. The results obtained indicated that the sample contained 5940 ppm potassium and 190 ppm lithium (by weight). This is equivalent to a molar ratio of 5.6 moles of potassium to 1 mole of lithium.

Example II

Production of 4-Methyl-1-Pentene with a Supported Benzyl Potassium Catalyst

A supported benzyl potassium was prepared using a procedure similar to the procedure in Example I except that the benzyl potassium was precipitated in the presence of a potassium carbonate ($K_2CO_3$) support. This catalyst system had approximately 4 grams of benzyl potassium on 65 grams of potassium carbonate.

Approximately 53 grams of the catalyst formed above was placed in a one liter, stainless steel reactor. The reactor was then pressurized to about 1400 psig. This pressure was maintained through the reaction. The reactor was also heated to a temperature of about 155° C. This temperature was also maintained through the reaction. After these pressures and temperatures were obtained, propylene was pumped into the reactor at a rate of five milliliters per minute. A Hewlitt Packard 5890 chromatograph, equipped with a capillary column and a liquid sampling valve, was attached to the reactor in order to sample the reactor effluent. The data below in Table EII represents the analysis of a liquid sample taken after the reaction was allowed to proceed for 4 hours.

TABLE EII

| Analysis of Liquid Sample | |
|---|---|
| Substance | Weight Percent |
| Propylene | 97.202 |
| $C_3$–$C_{12}$ | 0.273 |
| 4-methyl-1-pentene | 2.336 |
| 4-methyl-2-pentene | 0.189 |

It can be seen from the above data that the total propylene conversion was 2.798 weight percent. This gives a 4-methyl-1-pentene product to propylene converted ratio of about 83% (2.336/2.798). Furthermore, the 4-methyl-1-pentene to 4-methyl-2-pentene ratio is about 12:1. This is especially important considering the difficulty in separating 4-methyl-1-pentene from 4-methyl-2-pentene.

Example III

Production of Isobutylbenzene and 4-Methyl-1-Pentene from an in situ Benzyl Potassium Catalyst A one liter stainless steel reactor was used for this reaction. First, under a nitrogen purge, the following components were added to the reactor.

1) 300 milliliters of toluene;

2) 3.332 grams of potassium t-butoxide in 50 milliliters of toluene;

3) 15 milliliters of 2 molar n-butyl lithium.

The reactor was then pressurized to 100 psig with nitrogen. Subsequent to this pressurization the reactor's pressure was reduced to 20 psig. The heat was then turned on and 300 milliliters of propylene was then added to the reactor. The reaction conditions are indicated below in Table EIIIA.

TABLE EIIIA

| Reaction Conditions | | |
|---|---|---|
| Elapsed Time (minutes) | Temperature (°C.) | Pressure (psig) |
| 0 | 81.5 | N.R. |
| 2 | 98.9 | 350 |
| 10 | 112.1 | 405 |
| 21 | 130.0 | 490 |
| 28 | 131.6 | 495[1] |
| 112 | 125.5 | 460 |
| 142 | 130.1 | 480 |
| 180 | 129.2 | 475 |
| 228 | 127.4 | 465 |

Footnotes to Table EIIIA
[1]This was the peak temperature and pressure. The temperature controller was set at 122° C. However, the reactor's temperature kept rising until this peak temperature and pressure was obtained.
N.R. = Not Recorded.

At the end of the time period a liquid sample was obtained from the reactor and analyzed using a Hewlitt Packard 5890 chromatograph. The data is presented in Table EIIIB below.

TABLE EIII B

| Analysis of Liquid Sample | |
|---|---|
| Substance | Weight Percent[1] |
| Isobutylbenzene | 67 |
| n-butylbenzene | 2 |
| Methylindane | 19 |
| 4-methyl-1-pentene | 12 |

Footnotes to Table EIII B
[1]These weight percents are based on the products only. The amounts of toluene and propylene were not included in these calculations.

It can be seen from the above data that isobutylbenzene, which is a precursor to ibuprofen, was 67% of the product sampled. Furthermore it should be noted that 4-methyl-1-pentene was approximately 12% of the product sample. This was particularly interesting because there was substantially no 4-methyl-2-pentene formed during this reaction.

That which is claimed is:

1. A process to produce isobutylbenzene consisting essentially of:

contacting n-butyl lithium and potassium t-butoxide in the presence of toluene and propylene and recovering said isobutylbenzene.

2. A process to produce a single alkene addition product said process comprising contacting:

a hydrocarbyl lithium; with an alkali metal hydrocarbyloxide wherein said alkali metal is selected from the group consisting of sodium, potassium, cesium, rubidium, and mixtures of two or more thereof;

in the presence of an aromatic compound wherein said aromatic compound has the following formula

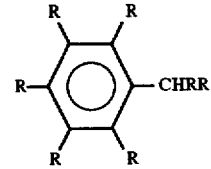

wherein each R group is independently selected from the group consisting of hydrogen, alkyl radicals, aryl radicals, and alkylaryl radicals; and in the presence of an alpha-olefin; and recovering said single alkene addition product.

3. A process according to claim 2 wherein said contacting is carried out in the presence of a catalytic support.

4. A process according to claim 3 wherein said catalytic support is selected from the group consisting of alkali metal carbonates, silicas, aluminas, silica-aluminas, alumina-phosphates and mixtures of two or more thereof.

5. A process according to claim 3 wherein said catalytic support consists essentially of potassium carbonate.

6. A process according to claim 2 wherein said hydrocarbyl lithium is selected from the group consisting of methyl lithium, ethyl lithium, propyl lithium, butyl lithium, pentyl lithium, hexyl lithium, and mixtures of two or more thereof.

7. A process according to claim 2 wherein said hydrocarbyl lithium consists of n-butyl lithium.

8. A process according to claim 2 wherein said alkali metal hydrocarbyloxide is selected from the group consisting of sodium methoxide, sodium ethoxide, potassium methoxide, potassium ethoxide, potassium propyloxide, potassium butoxide, potassium pentoxide, and mixtures of two or more thereof.

9. A process according to claim 2 wherein said alkali metal hydrocarbyloxide consists essentially of potassium butoxide.

10. A process according to claim 2 wherein said aromatic compound is selected from the group consisting of toluene, 1,2-dimethyl benzene, 1,3-dimethyl benzene, 1,4-dimethyl benzene, 1,3,5-trimethyl benzene, and mixtures of two or more thereof.

11. A process according to claim 2 wherein said aromatic compound consists of toluene.

12. A process according to claim 2 wherein said alpha-olefin is selected from the group consisting of ethylene, propylene, 1-butene, isobutylene, 3-methyl-1-butene, 1-pentene, 3-methyl-1-pentene, 4-methyl-1-pentene, 1-hexene, 3-ethyl-1-hexene, 1-octene, 1-decene, and mixtures of two or more thereof.

13. A process according to claim 2 wherein said alpha-olefin consists of propylene.

14. A process according to claim 3 wherein said catalytic support consists essentially of silica-alumina.

* * * * *